United States Patent
Wohlschlager et al.

(10) Patent No.: US 11,583,256 B2
(45) Date of Patent: Feb. 21, 2023

(54) FAT LAYER DEPENDENT SENSOR ADAPTATION

(71) Applicant: KONINKLIJKE PHILIPS N.V., Eindhoven (NL)

(72) Inventors: Markus Wohlschlager, Sindelfingen (DE); Hansjoerg Geywitz, Kusterdingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 673 days.

(21) Appl. No.: 16/305,077

(22) PCT Filed: Jun. 20, 2017

(86) PCT No.: PCT/EP2017/065339
§ 371 (c)(1),
(2) Date: Nov. 28, 2018

(87) PCT Pub. No.: WO2018/001843
PCT Pub. Date: Jan. 4, 2018

(65) Prior Publication Data
US 2020/0375577 A1    Dec. 3, 2020

(30) Foreign Application Priority Data
Jun. 27, 2016 (EP) .................................. 16176493

(51) Int. Cl.
*A61B 8/00* (2006.01)
*A61B 5/00* (2006.01)
(Continued)

(52) U.S. Cl.
CPC .............. *A61B 8/54* (2013.01); *A61B 5/0035* (2013.01); *A61B 5/0075* (2013.01);
(Continued)

(58) Field of Classification Search
CPC ....... A61B 8/488; A61B 8/565; A61B 5/7264; A61B 5/4872; A61B 5/4362;
(Continued)

(56) References Cited

U.S. PATENT DOCUMENTS

| 4,785,817 A | * | 11/1988 | Stouffer | ............... | A22B 5/007 |
| | | | | | 600/443 |
| 5,520,183 A | | 5/1996 | Lake | | |

(Continued)

FOREIGN PATENT DOCUMENTS

| CA | 2397611 | 7/2002 |
| CN | 203379137 U | 1/2014 |

(Continued)

OTHER PUBLICATIONS

D. Cavouras, et al., "Computer Image Analysis of Ultrasound Images for Discriminating and Grading Liver Parenchyma Disease Employing a Hierarchical Decision Tree Scheme and the Multilayer Perceptron Neural Network Classifier," Medical Informatics Europe, pp. 522-526. 1997 (Year: 1997).*

(Continued)

*Primary Examiner* — Joel Lamprecht
*Assistant Examiner* — Nyrobi Celestine (57) ABSTRACT

The present invention is directed to a method for health monitoring using one or more sensors comprising first measuring (100) a body composition via one or more sensors. The measured body composition is then classified (102) into one of a plurality of categories. An at least one setting to be used for the health monitoring is adjusted (104) based on the classified body composition. Then, the health monitoring is performed (106) using the adjusted at least one health monitoring setting, wherein at least one of the sensors used to measure the body composition may also be used to perform the health monitoring.

11 Claims, 6 Drawing Sheets

(51) Int. Cl.
*A61B 5/107* (2006.01)
*A61B 8/08* (2006.01)

(52) U.S. Cl.
CPC .......... *A61B 5/1075* (2013.01); *A61B 5/1079* (2013.01); *A61B 5/4362* (2013.01); *A61B 5/4872* (2013.01); *A61B 5/7264* (2013.01); *A61B 8/0858* (2013.01); *A61B 8/4494* (2013.01); *A61B 8/461* (2013.01); *A61B 8/488* (2013.01); *A61B 8/5223* (2013.01); *A61B 8/565* (2013.01)

(58) Field of Classification Search
CPC ....... A61B 5/0035; A61B 5/0075; A61B 8/54; A61B 5/1075; A61B 8/0858; A61B 5203/02; A61B 8/0866; A61B 5/4356; A61B 5/1079; A61B 5/0059
See application file for complete search history.

(56) References Cited

U.S. PATENT DOCUMENTS

| | | | |
|---|---|---|---|
| 5,941,825 A | 8/1999 | Lang | |
| 6,280,381 B1 | 8/2001 | Malin | |
| 6,512,937 B2 | 1/2003 | Blank et al. | |
| 8,057,465 B2* | 11/2011 | Sliwa, Jr. | A61N 1/06 606/27 |
| 8,109,874 B2* | 2/2012 | Kong | G16H 40/63 600/300 |
| 8,357,094 B2* | 1/2013 | Mo | A61B 8/00 600/438 |
| 8,764,651 B2* | 7/2014 | Tran | A61B 5/1112 600/300 |
| 2001/0021803 A1 | 9/2001 | Blank et al. | |
| 2004/0267252 A1 | 12/2004 | Washington et al. | |
| 2007/0239070 A1 | 10/2007 | Hwang | |
| 2009/0270728 A1* | 10/2009 | Da Silva | A61B 5/4869 600/437 |
| 2010/0030111 A1* | 2/2010 | Perriere | A61B 5/150389 600/583 |
| 2010/0036246 A1 | 2/2010 | Kushculey | |
| 2010/0274145 A1* | 10/2010 | Tupin, Jr. | A61B 5/4362 600/511 |
| 2012/0215109 A1* | 8/2012 | Kubota | A61B 5/4872 600/443 |
| 2013/0281861 A1 | 10/2013 | Flomerfelt | |
| 2014/0228653 A1 | 8/2014 | Kiraly | |
| 2014/0276070 A1* | 9/2014 | Kabakov | A61B 5/02411 600/453 |
| 2014/0343419 A1* | 11/2014 | Sako | A61B 8/5292 600/437 |
| 2016/0074017 A1 | 3/2016 | Lee et al. | |

FOREIGN PATENT DOCUMENTS

| | | | |
|---|---|---|---|
| EP | 1844707 | | 10/2007 |
| JP | H03165748 A | | 7/1991 |
| JP | H047650 A | | 3/1992 |
| JP | 2006110347 A | | 4/2006 |
| JP | 2007020730 A | * | 2/2007 |
| JP | 2007301035 A | | 11/2007 |
| JP | 2008188077 A | * | 8/2008 |
| JP | 2009077754 A | * | 4/2009 |
| JP | 2015/037472 | | 2/2015 |
| JP | 2015037472 A | * | 2/2015 |
| KR | 20100075020 A | * | 7/2010 |
| WO | 2012/142493 | | 10/2012 |
| WO | 2015120540 | | 8/2015 |

OTHER PUBLICATIONS

E. Tafeit, et al., "Artificial neural networks as a method to improve the precision of subcutaneous adipose tissue thickness measurements by means of the optical device LIPOMETER," Computers in Biology and Medicine, vol. 30, pp. 355-365, Mar. 2000 (Year: 2000).*

B. Bhindi, et al., "Measurement of peri-prostatic fat thickness using transrectal ultrasonography (TRUS): a new risk factor for prostate cancer," BJU International, vol. 110, pp. 980-986, Nov. 2011 (Year: 2011).*

E. B. Gur, et al., "Ultrasonographic visceral fat thickness in the first trimester can predict metabolic syndrome and gestational diabetes mellitus," Endocrine, vol. 47, pp. 478-484, Jan. 2014 (Year: 2014).*

G. De Pergola, et al., "Para—and perirenal ultrasonographic fat thickness is associated with 24-hours mean diastolic blood pressure levels in overweight and obese subjects," BMC Cardiovascular Disorders, vol. 15, No. 108, pp. 1-7, Sep. 2015 (Year: 2015).*

A. D. Mitchell et al., "Estimation of body composition of pigs by a near-infrared interactance probe technique", Archiv fur Tierzucht, vol. 48, No. 6, pp. 580-591, Oct. 2005 (Year: 2005).*

JP-2007020730-A (Year: 2007).*

Dale R. Wagner, "Ultrasound as a Tool to Assess Body Fat," Journal of Obesity, vol. 2013, Article ID 280713, 9 pages, 2013.

Azizian, et al., "First Direct Body Fat Content Measurement During Pregnancy Using Fourier Transform Near-Infrared Spectroscopy," Appl. Spectrosc.68, 379-382 (2014). doi:10.1366/13-07256.

* cited by examiner

FAT LAYER DEPENDENT SENSOR ADAPTATION

CROSS REFERENCE TO RELATED APPLICATIONS

This application is the U.S. National Phase application under 35 U.S.C. § 371 of International Application No. PCT/EP2017/065339, filed Jun. 22, 2017, published as WO 2018/001843 on Jan. 4, 2018, which claims the benefit of European Patent Application Number 16176493.1 filed Jun. 27, 2016. These applications are hereby incorporated by reference herein.

BACKGROUND OF THE INVENTION

Monitoring fetal and maternal physiological parameters during labor and delivery require highly sensitive sensor elements for obtaining accurate signals. Specifically, body fat negatively affects the measurability of many physiological parameters recorded during labor and delivery. With the increasing number of overweight patients, obtaining accurate signals is becoming a challenge.

Some fetal monitors offer manual means for sensitivity adjustments according to the patient's body constitution. For example, sensor sensitivity during uterine contraction measurements can be reduced by 50% in order to avoid clipping of the recording when the sensor is applied to slim women. However, these types of sensor sensitivity adjustment means are usually manually operated. Because of this, the adjustment process is both time consuming and error-prone. In addition, operators must have sufficient knowledge, skill, and experience before they can consistently optimize the needed adjustments in order to obtain accurate measurements. Thus, an automated evaluation of the patient's body constitution coupled with an automatic sensitivity adjustment means would provide a more efficient workflow for a typical fetal monitoring session. It could also dramatically enhance the reliability and accuracy of the measurement because the signal acquisition and processing are performed using optimized measurement parameters.

Various methods for body fat layer thickness measurements are known. The most popular methods are based on ultrasound pulse echo duration evaluation, near infrared spectroscopy (NIRS), or measurement of the electrical body impedance. Most of these methods involve special devices specifically designed to measure body fat percentage. Hence, the obtained body fat thickness measurements cannot be directly used to make the necessary adjustments to the fetal monitoring sensors during fetal monitoring. It would therefore be advantageous to develop a quick and simple means to classify a patient's body constitution or fat layer thickness by doing away with the need to use additional, separate sensors solely for body constitution measurements at the beginning of each fetal monitoring session.

One of the most common non-invasive fetal monitoring techniques involves the use of ultrasound Doppler transducers. Ultrasound Doppler transducers have two modes of operation, namely, continuous-wave Doppler and pulsed-wave Doppler. In continuous-wave Doppler mode, both the transmission and reception of sound waves are simultaneously detected. In pulsed-wave mode or pulse-echo mode, short bursts of sound waves are sent into the area under examination. The waves are reflected back as echoes, which are to be converted into signals that can be used to characterize the examined area. For external fetal heart monitoring, the pulsed-wave Doppler mode is more commonly used.

U.S. Pat. App. No. 2013/0281861 discloses an electronic external fetal monitoring (EFM) system designed for obese patients. It discloses the use of a more sensitive EFM system to allow for more sensitive ultrasound measurements. WO2015120540 discloses an FT-NIR based apparatus for measuring and monitoring the body fat percentages and body fat accretion in a female subject during pregnancy. The disclosed apparatus includes a computerized means for calculating the subject's body fat percent and fat mass through the use of a pre-determined calibration model or matrix.

SUMMARY OF THE INVENTION

The present specification is directed to a method for health monitoring using one or more sensors comprising measuring a body composition via one or more sensors provided at a measuring probe of a health monitoring device. The measured body composition is then classified into one of a plurality of categories, e.g. slim, normal and obese. At least one setting of the health monitoring is adjusted based on the body composition classification. Then, health monitoring is performed using the adjusted at least one setting.

A particular example of health monitoring in accordance with the present disclosure is fetal and maternal health monitoring during labor and delivery. The measurement of the body composition comprises measuring body fat thickness. The body fat thickness is preferably measured using an ultrasound Doppler sensor in a pulse echo mode, but could also be measured using a plurality of infrared sensors in the health monitoring device, or a combination of an ultrasound Doppler sensor and a plurality of infrared sensors provided at a measuring probe of a health monitoring device. The measuring probe may thus comprise one or more sensors or sensor arrays of the same or of different types housed in the same measuring probe of a health monitoring device. Preferably, the measuring probe may be an ultrasound transducer usable in different modes, with or without integrated infrared (IR) sensors.

In some implementations, an additional ultrasound channel may be integrated into a standard monitoring device working in pulse echo mode, the additional channel using the same or a different frequency to prevent interference. Such additional channel can be used exclusively for body composition measurement. This additional channel can consist of one or more elements integrated into the sensor module. Further, it can be integrated in any transducer. In some applications, a higher frequency may be utilized, such as for example about 7 MHz which is the smaller size of the PZT element (piezoelectric ceramic material) and therefore would allow for better integration into the health monitoring device. Thus, alternative implementations may combine piezo elements with different resonant frequencies. The higher the frequency, the smaller is the size of the piezo elements and thus easier integration into the hardware module. Keeping the two ultrasound systems independent from each other would add a damping measures in order to speed up the decay.

The method and systems outlined herein enhance signal detection by keeping the signal level, for example, by controlling the amplification gain (Toco 50%) depending on the body constitution. Since the fat layer is a sound energy absorber, the ultrasound pulses are attenuated and do not have sufficient energy after reflection without modification based upon body constitution. The method and system described also improves the accuracy of the physiological measurements because health monitoring settings are adjusted in accordance with the patient's determined body fat classification. Finally, the method and systems set forth are simple and convenient to perform because the sensor probe housing the one or more sensors or sensor arrays of the same or of different types which is used for the body composition measurement is also used for fetal monitoring.

In various embodiments, the system described herein may include a system for health monitoring, comprising: an ultrasound device in communication with a user device; the ultrasound device having a power source, communication module, memory, a processor and a transducer array, the transducer array having a plurality of transducer elements for receiving Doppler signals; the ultrasound device operable to convert received ultrasound information for transmission to the user device; wherein the user device includes processor, display and memory; wherein the user device has instructions in the user device memory which, when executed, operates to: receive the ultrasound information; determine a body classification from the received ultrasound information; transmit the body classification to the ultrasound device; wherein the ultrasound device modifies an operating parameter based upon the determined body classification.

In some implementations, the transducer array may include one or more transducer arrays operating at differing frequencies as noted herein. Further aspects may include transmission of the body classification to other transducers or to a base unit wherein operating parameters of other transducers attached to the patient may be modified.

These and other implementations may each optionally include one or more of the following features. For instance, the features may include wherein the ultrasound device modifies an operating parameter, the operating parameter at least one of ultrasound transmit energy, amplifier gain adaptation and depth setting. Additional features may include wherein the body classification is based upon fat layer thickness. Further features may include wherein the ultrasound device operates in a first mode to determine fat layer thickness and a second patient monitoring mode. Additional features may further include wherein the first mode is a pulse-echo mode and the second mode is a pulse Doppler mode. Some further features may also include wherein the ultrasound device further comprises: at least one IR sensor, the at least one IR sensor of the ultrasound device operable to obtain a body fat thickness signal, and wherein the user device is operable to receive the body fat thickness signal and modify the body classification based upon the body fat thickness signal. Further features may include wherein the at least one IR sensor is an IR receiver and an IR transmitter. Still further features may include wherein the user device has instructions in the user device memory which, when executed, operates to: determine an IR body fat thickness based upon the body fat thickness signal; determine an ultrasound body fat thickness based upon the received ultrasound information; calculate an average body fat thickness value based upon the ultrasound body fat thickness and the IR body fat thickness; determine the body classification based upon the average body fat thickness.

In various embodiments, the method described herein may include measuring a body composition via one or more sensors on an ultrasound device; classifying the measured body composition into one of a plurality of categories; adjusting an at least one setting to be used on the ultrasound device for the health monitoring based on the classified body composition; performing the health monitoring using the ultrasound device based upon the adjusted at least one health monitoring setting.

These and other implementations may each optionally include one or more of the following features. For instance, some features may include further implementing: measuring a fat layer thickness data by the ultrasound device; transmitting data representing said fat layer thickness data to a user device; comparing the fat layer thickness data with predetermined fat layer thickness thresholds to derive the measured body composition. Additional features may include measuring of the fat layer thickness data is conducted with ultrasound reflection. Still further features may include measuring of fat layer thickness data is conducted with IR reflection. Additional features may include the measuring of fat layer thickness data is conducted with IR reflection and ultrasound reflection. Still further features may include modifications wherein the adjusted at least one health monitoring setting includes at least one of ultrasound transmit energy, amplifier gain adaptation or depth settings.

Other aspects may include corresponding methods, systems, apparatus, and computer program products.

Other implementations may include one or more non-transitory computer readable storage media storing instructions executable by a processor (e.g., a central processing unit (CPU) or graphics processing unit (GPU)) to perform a method such as one or more of the methods described above. Yet another implementation may include a system of one or more computers that include one or more processors operable to execute stored instructions to perform a method such as one or more (e.g., all) aspects of one or more of the methods described above.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

BRIEF DESCRIPTION OF THE DRAWINGS

The accompanying drawings, which are included to provide a further understanding of the disclosure, are incorporated herein to illustrate various embodiments. In the drawings.

DETAILED DESCRIPTION OF EMBODIMENTS

In some implementations of the technology described and disclosed herein, a method and system are provided for monitoring health using one or more sensors. The one or more sensors may be operable to classify measured body compositions into one of a plurality of categories. After classification, the method and system may as well adjust and modify the operation of a health monitoring device such that the settings of the device are based upon the classified body composition. Once such setting is adjusted and modified, the system and method allow for performance of the health monitoring using the adjusted at least one health monitoring setting wherein the sensors used to measure body composition is also used to perform the health monitoring.

The following are terms used in the description for the various embodiments set out herein.

The term "sensor" as used herein may in some aspects refer to the ultrasound device component that is used to monitor the fetal and maternal physiological parameters. An example of a "sensor" as used herein is a transducer, such as an ultrasound transducer.

The term "health monitoring" as used herein may in some aspects refer to the monitoring or measurement of a patient's physiological parameters such as those performed during pregnancy, labor and delivery. The systems used for health monitoring include devices such as an ultrasound device.

The technology disclosed herein relates to a method for health monitoring using one or more sensors. The method comprises: measuring a body composition via one or more sensors; classifying the measured body composition into one of a plurality of categories; adjusting at least one setting to be used for the health monitoring based on the classified body composition; and performing the health monitoring using the adjusted at least one health monitoring setting, wherein at least one of the sensors used to measure the body composition is also used to perform the health monitoring.

Figure 1:
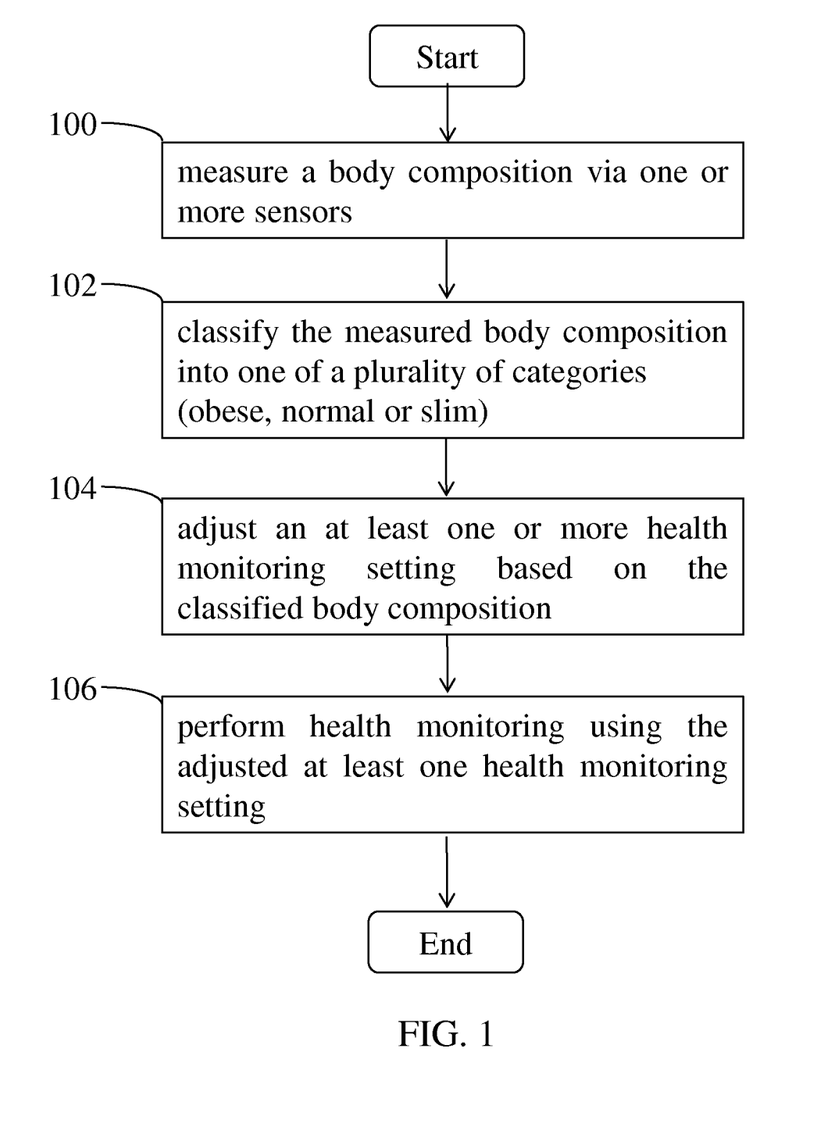
FIG. 1 is a flowchart illustrating a method for health monitoring using one or more sensors according to one embodiment of the disclosure set forth herein.

FIG. 1 is a flowchart illustrating a method for health monitoring using one or more sensors according to an embodiment of the present disclosure. A patient's body composition is measured via one or more sensors (step 100). The body composition to be measured is preferably body fat, but could also be muscle, bone or body water or the distance between the transducer surface and the amniotic sac. The body composition measurement is in some embodiments obtained using ultrasound Doppler sensors. Alternatively, infrared sensors could also be used to obtain body fat thickness measurements. Preferably, the body composition could be measured by measuring the tissue layer (including the fat layer), due to the significant and clear reflection signal of the amniotic sac. Using for instance an ultrasoundtransducer with a non backed piezo element, the detection of the transition between the tissue and the amniotic sac is easier than measuring the fat layer alone. The measured body composition is then used to classify the patient's fat layer thickness into one of a plurality of categories (step 102). In one embodiment, the categories include "OBESE," "NORMAL," or "SLIM." After the body composition has been classified, an at least one health monitoring setting is then adjusted based on the body composition classification (step 104). The one or more health monitoring setting that may be adjusted according to the present invention include ultrasound transmit energy, amplifier gain adaptation, and depth settings, among others. Afterwards, health monitoring is performed using the adjusted at least one health monitoring setting, wherein at least one of the sensors used to measure the body composition is also used to perform the health monitoring (step 106). An example of health monitoring includes fetal monitoring or maternal health monitoring preferably during labor or delivery. Alternatively, the health monitoring is performed for regular pregnancy checkups.

In some implementations, a health system, such as a fetal monitoring system, may integrate a number of sensors which are applied at the same time, such as for instance Sp02, blood pressure or non-invasive blood pressure, temperature or uterine activity. Such sensors, collectively, may be in influenced by fat layers of the patient to prevent accurate readings. Thus, in some aspects, upon classify the patient's fat layer thickness into one of a plurality of categories, the classification may be broadcast on a communication channel or subsystem between devices so that similar adjustments may be made to the measuring device based upon such classification. In even further aspects, where a number of transducers or other devices are implemented to measure patient health and each is capable of measuring or determining body composition, a communication subsystem existing between the modules may be utilized to share respective composition determinations. In such instance, one or more broadcasted value of patient body compositions may be correlated by the individual sensors or health monitoring system for cross checking and consolidation.

Figure 2:
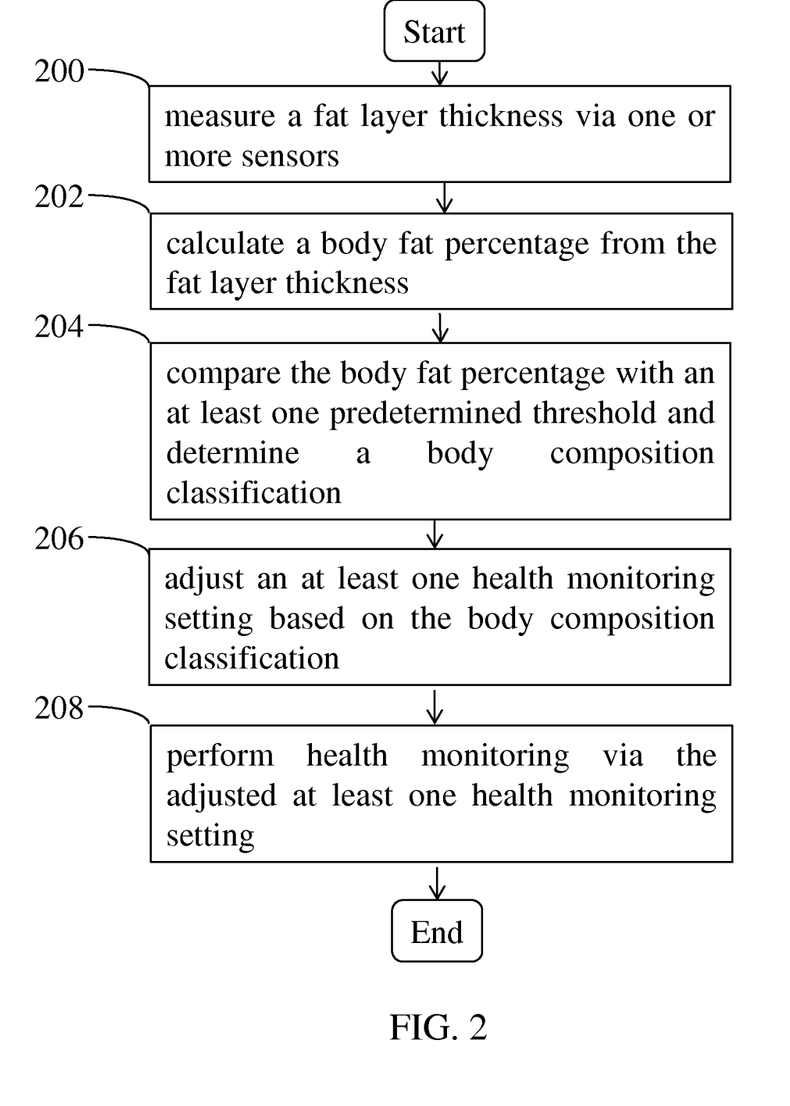
FIG. 2 is a flowchart illustrating a method for adjusting an at least one health monitoring setting according to an embodiment of the disclosure set forth herein.

FIG. 2 is a flowchart illustrating a method for adjusting an at least one health monitoring setting according to one aspect of the present disclosure. A body fat layer thickness is measured via one or more sensors (step 200). The body fat layer thickness is in some embodiments obtained using ultrasound Doppler sensors, but could alternatively be measured using infrared sensors in other embodiments, such as those sold under the Philips brand. The measured body fat layer thickness is then used by a user device to calculate a body fat percentage (step 202). The calculated body fat percentage may then be compared with an at least one predetermined body fat threshold to determine a body fat composition classification (step 204). Body fat thresholds are preferably set in accordance with the American Council on Exercise standard, wherein a body fat percentage of 24% and below is classified as "SLIM," 25-31% body fat is classified as "NORMAL," and above 32% is classified as "OBESE." Alternatively, body fat thresholds may be set using body mass index (BMI) World Health Organization (WHO) standard instead of body fat percentage. In this case, a BMI less than 18.5 kg/m$^2$ is classified as "SLIM," a BMI between 18.5 to 24.9 kg/m$^2$ is classified as "NORMAL," and a BMI that is greater than 30 kg/m$^2$ is classified as "OBESE." Such derived value, once determined, may in various implementations be transmitted or broadcast across a communication subsystem to singular or multiple devices to be used in the health monitoring system. An at least one health monitoring setting is then adjusted based on the determined body composition classification (step 206). Afterwards, health monitoring is performed via the adjusted at least one health monitoring setting, wherein at least one of the sensors used to measure the body composition is also used to perform the health monitoring (step 208).

Figure 3:
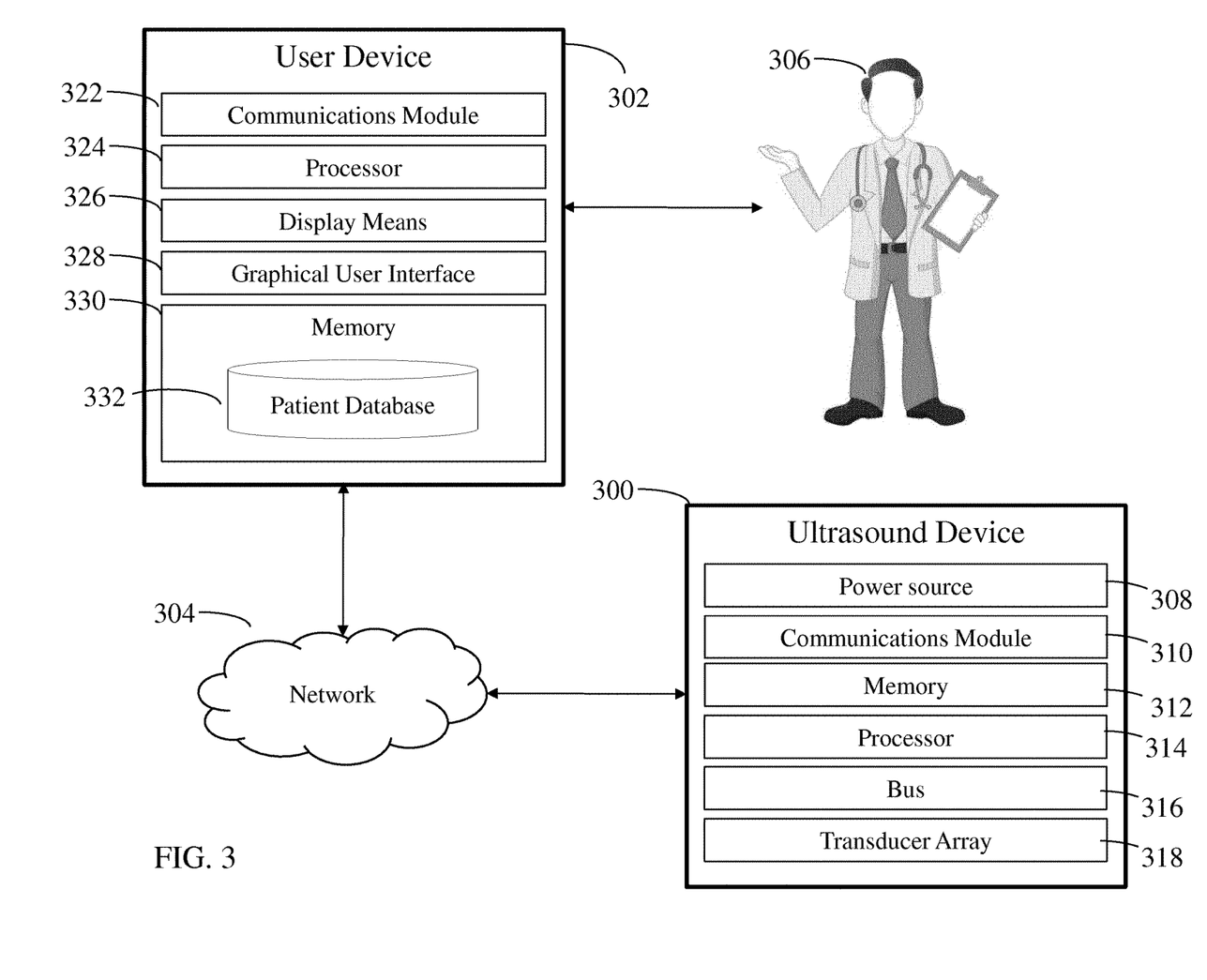
FIG. 3 shows a system for measuring body fat thickness during a fetal monitoring session according to an embodiment of the disclosure set forth herein.

FIG. 3 shows a system for measuring body fat thickness during a fetal monitoring session, according to an alternative embodiment of the present disclosure. The system comprises an ultrasound device 300, a user device 302, a network 304, and a user 306. The ultrasound device 300 comprises a power source 308, communications module 310, memory 312, processor 314, bus 316, and transducer array 318. The transducer array 318 comprises a plurality of transducer elements preferably arranged in a circular fashion, with an at least one transducer element may be positioned at the center of the array. The transducer elements are optionally piezoelectric transducers or alternative sources of transducers. Hence, in various embodiments of the system, multiple transducers may be utilized to obtain readings for classification which may then be averaged, correlated or verified. The various transducer sources may forward readings to the user device or other networked computer for computational analysis of the patient composition which is then transferred throughout or broadcast throughout the system. As shown in this embodiment, the transducer array 318 receives Doppler signals via the communications module 310, through either wired cables or wireless connection means. Thus, as depicted in FIG. 3, the ultrasound device could receive not only a single source for measuring body composition but multiple sources.

The communications module 310 may enable communication between the ultrasound device 300 and a user device 302 via network 304 or from multiple transducers in the system. The communications module 310 can be a physical channel such as a Universal Serial Bus (USB) cable or other wired forms of communication. Alternatively, the communications module 310 can be any transmitter or receiver used for Wi-Fi, Bluetooth, infrared, NFC, radio frequency, cellular communication, visible light communication, Li-Fi, WiMax, ZigBee, fiber optic, and other types of wireless communication devices. The power source 308 may be any rechargeable battery for meeting the power requirements of the ultrasound device 300. The battery preferably can be charged using both wired and wireless charging methods.

The bus 316 is a circuit that serves as a connection between the aforementioned components and allows communications among them. The processor 314 may be any hardware device capable of issuing instructions, executing calculations, or processing data. As such, the processor may include a microprocessor, field programmable gate array (FPGA), application-specific integrated circuit (ASIC), or other similar devices. The processor 314 may receive and in some aspects evaluate requests or commands from the device components and performs data processing or operation based on the evaluated requests or commands. In one embodiment, the processor 314 preferably converts received ultrasound wave packets to signals suitable for transmission to a user device. The memory 312 may include various memory types such as cache or system memory. As such, the memory 312 may include static random access memory (SRAM), dynamic RAM (DRAM), flash memory, read only memory (ROM), or other similar memory devices.

The user device and the health monitoring device or ultrasound device may include a separate processor with associated memory to allow for execution of programs implementing various features and functions of both units described herein. In some aspects, determination of body composition and/or fat layer thickness may be completed by either of the user device 302 or the ultrasound device 300 and/or may execute programs from the same memory to accomplish such functions. Further, in various implementations, the patient database may be accessible by one or both the user device and the ultrasound device. Additionally, a separate display and or user interface may be integrated with the user device and or the ultrasound device. The various structures of the system described herein may further include shared memory and database access.

The user interface may further include a display subsystem. The display subsystem may include a cathode ray tube (CRT), a flat-panel device such as a liquid crystal display (LCD), a projection device, or some other mechanism for creating a visible image. The display subsystem may also provide non-visual display such as via audio output devices.

In general, use of the term output device and display/user interface is intended to include all possible types of devices and ways to output information from computing device to the user or to another machine or computing device.

Further, in some aspects, a storage subsystem may be used with the memory to store programming and data constructs that provide the functionality of some or all of the modules described herein including the database. For example, a storage subsystem or other memory may include the logic to perform one or more aspects of the various methods described.

The software modules which implement the various features set out in the implementations are generally executed by a processor alone or in combination with other processors. Both the user device and the ultrasound device may include a separate processor with associated memory to allow for execution of programs implementing the various features and functions of the ultrasound unit and the user interface of the user device. In some aspects, both the health monitoring device/ultrasound device and the user device may be integrated in the same module and/or may execute programs from the same memory. Memory used in the various storage subsystems can include a number of memories including a main random access memory (RAM) for storage of instructions and data during program execution and a read only memory (ROM) in which fixed instructions are stored. A file storage subsystem may further be used to provide persistent storage for program and data files, and may include various known implementations for digital and electronic storage such as a hard disk drive, etc. The software modules implementing the functionality of certain implementations may be stored by the file storage subsystem in the storage subsystem, or in other machines accessible by the processor(s) described herein.

The user device 302 includes a communications module 322, processor 324, display means 326, graphical user interface (GUI) 328, and memory 330. The user device 302 can be any computing device such as a laptop, smartphone, or tablet, among others.

The memory 330 comprises a patient database 332, which stores patient-related information and data, such as patients' personal information, ultrasound test results and images, and other laboratory test results, among others. The graphical user interface 328 includes one or more devices for enabling communication with a user. For example, the graphical user interface 328 may include a display, a mouse, a keyboard, a touchscreen, buttons, camera, microphone, vibrator, haptic engine, etc.

Figure 4:
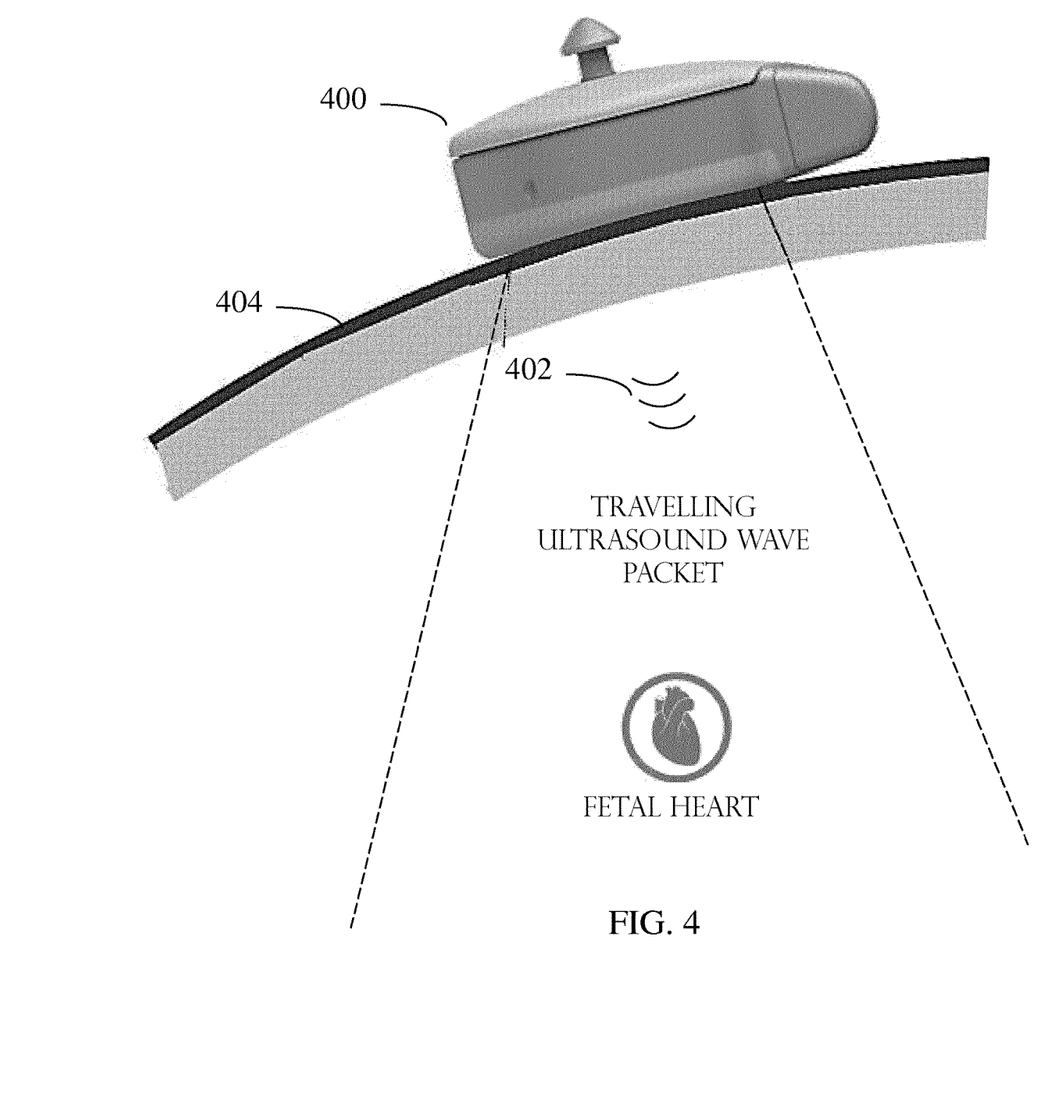
FIG. 4 illustrates a method for measuring fat layer thickness during a fetal monitoring session using the pulse-echo mode of a standard Doppler ultrasound sensor.

FIG. 4 illustrates an embodiment including a method for measuring fat layer thickness during a fetal monitoring session using the pulse-echo mode of the standard Doppler ultrasound sensor. The transducer element 400 is switched from pulsed Doppler mode to pulse-echo mode at the start of the monitoring session. The transducer element 400 transmits an at least one ultrasound wave packet 402 towards a patient's abdomen. When the at least one ultrasound wave packet 402 comes in contact with a fat layer surface 404 in the patient's abdomen, the at least one ultrasound wave packet 402 is reflected back and received by the transducer element as an echo. The received at least one ultrasound wave packet 402 is then converted into electrical signals. The electrical signals are then transmitted to the user device via an at least one channel. The user device then processes the transmitted signals and generates an A-mode ultrasound reflection amplitude graph. A fat layer thickness is then calculated from the A-mode ultrasound reflection amplitude graph, as represented by the shaded region. The obtained fat thickness layer measurement is then compared with fat layer thickness thresholds to derive a patient body fat classification (e.g., "OBESE," "NORMAL," or "SLIM"). The user device transmits the derived body classification to the ultrasound device or other devices within the system/network, which then adjusts an at least one health monitoring setting based on the received body fat classification. After adjusting at least one health monitoring setting, the ultrasound device is switched back to pulsed Doppler mode and health monitoring is performed using the at least one adjusted health monitoring setting.

Figure 5:
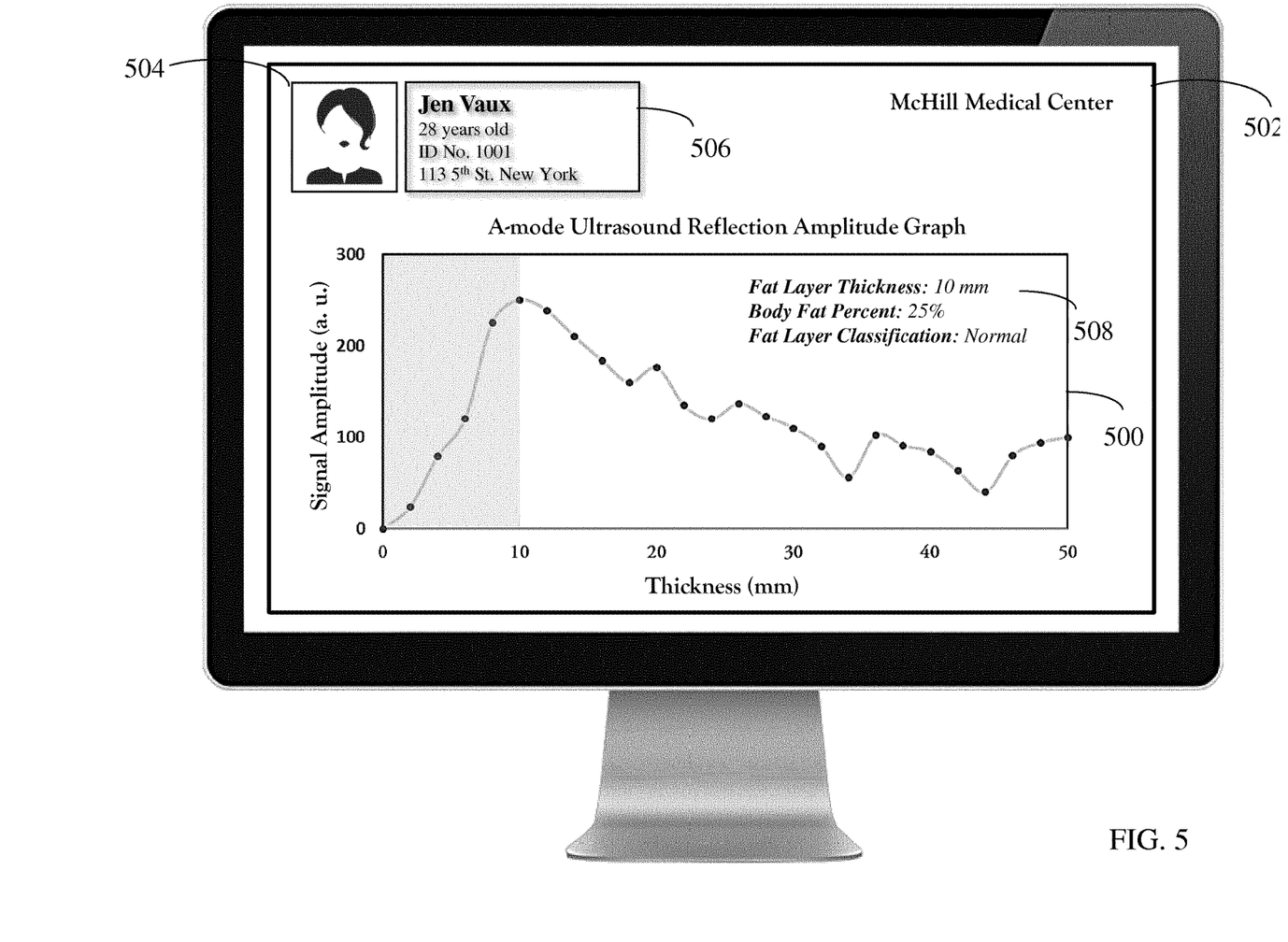
FIG. 5 is a screenshot of a user device graphical user interface (GUI) that shows an A-mode ultrasound reflection amplitude graph from an abdominal scan and the corresponding body fat classification.

FIG. 5 is a screenshot of a user device graphical user interface (GUI) that shows A-mode ultrasound reflection amplitude graph 500 from an abdominal scan. The GUI 502 shows a patient image 504, a window 506 showing a patient's personal information, another window 508 indicating a body fat classification, and an A-mode ultrasound reflection amplitude graph 508 from an abdominal scan. Window 506 comprises the patient's image, patient's name, age, and patient ID number. Window 508 shows that the patient has a fat layer thickness of 10 mm, body fat percentage of 25%, and a "NORMAL" body fat classification. In the A-mode ultrasound reflection amplitude graph 500, the y-axis represents the signal amplitude, while the x-axis represents the tissue depth. As FIG. 5 shows, the fat layer thickness is determined by identifying the thickness (in this case 10 mm) along the x-axis that corresponds to the highest peak in the plot (corresponding to the highest intensity signal received from the reflected IR beam).

Figure 6:
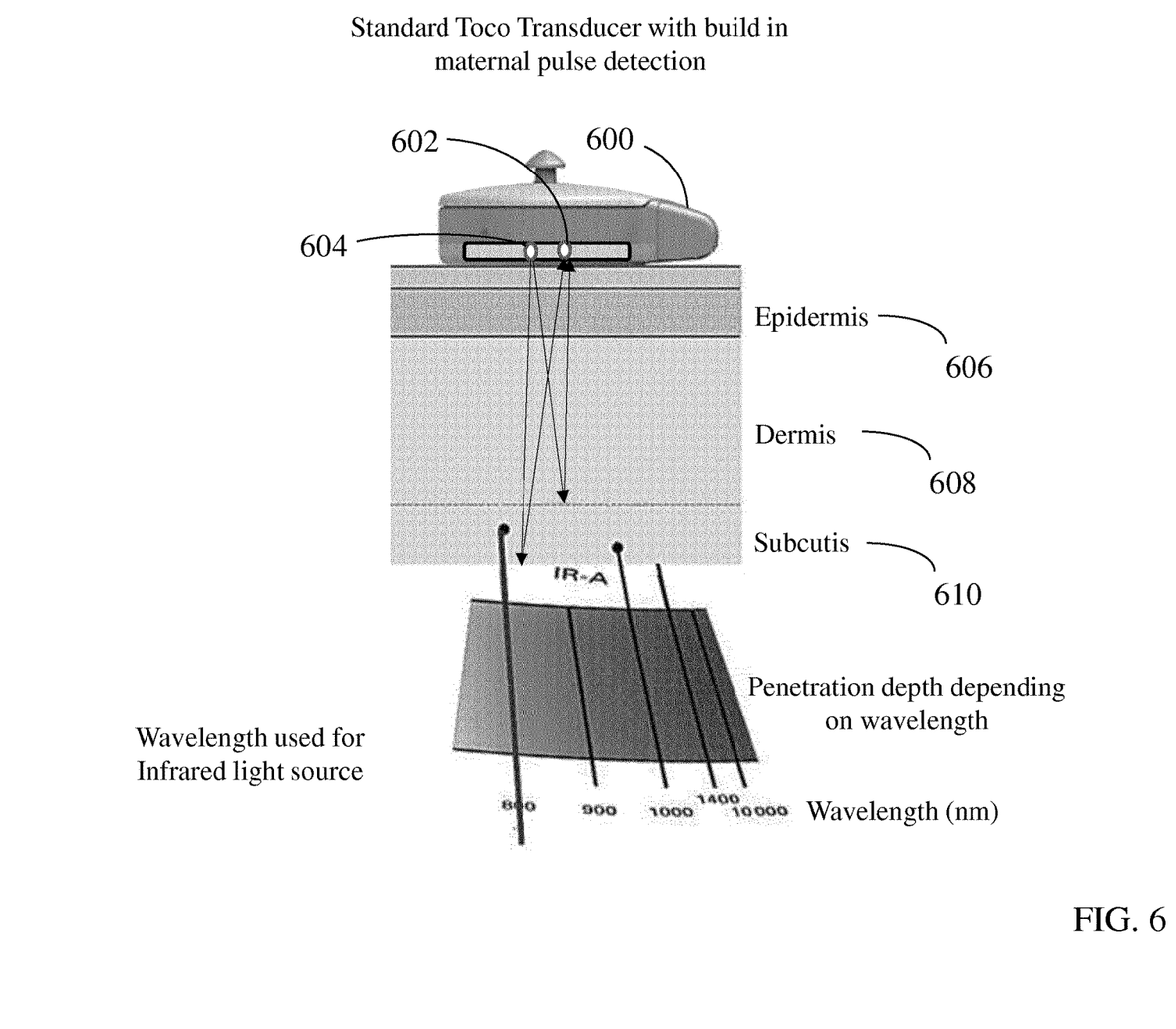
FIG. 6 illustrates a method for measuring fat layer thickness during a fetal monitoring session using infrared sensors.

FIG. 6 illustrates a method for measuring fat layer thickness during a fetal monitoring session using infrared sensors integrated into a Toco device 600 according to various aspects disclosed herein. Measurement of fat layer thickness using infrared light sources is conducted. Toco, as known, is a pressure-sensitive contraction transducer, called a tocodynamometer and generally has a flat area that is fixated to the skin by a band around the belly. The pressure required to flatten a section of the wall correlates with the internal pressure, thereby providing an estimate of the contraction. The integrated IR sensors may be of two types: an IR receiver 602 and an IR transmitter 604. The Toco sensor 600 sits on top of a skin layer which includes an epidermis 606, a dermis 608, and a subcutis 610, which is the fat tissue layer. The IR transmitter 604 directs IR waves towards the fat tissue which reflects the signal dependent on the wavelength. The reflected IR is returns back to the device and reaches the IR receiver 602 which is detected. The shifts in the IR can indicate the various depths of fat tissue within the patient. Also, as shown in FIG. 6, the depth of penetration of the tissue by the transmitted IR depends on the specific IR wavelength used, so different IR wavelengths will penetrate the fat tissue to different extents. Thus, the wavelength shift corresponding to the top layer of the fat tissue and the wavelength shift corresponding to the bottom layer of the fat tissue can provide a measure of the fat layer thickness. The calculated fat layer thickness is then used to compare with fat layer thickness thresholds and to derive a patient body fat classification ("OBESE," "NORMAL," or "SLIM"). The user device then sends a signal to the ultrasound device which corresponds to the body fat classification. Afterwards, the health monitoring device, such as an ultrasound device adjusts an at least one health monitoring setting based on the received signal.

In one embodiment, a patient visits a clinic for fetal heart rate monitoring. At the start of the session, an attending physician initially sets an ultrasound device to pulse-echo mode. The attending physician then begins body fat layer thickness measurement using the ultrasound device for determination of composition or layer thickness. A computer monitor displays in real-time the reflected ultrasound echoes of the fat tissue in two modes—amplitude mode (A-mode) and brightness mode (B-mode). The A-mode graph shows the signal amplitude versus tissue depth in a single dimension. A fat layer thickness is calculated from the A-mode ultrasound reflection amplitude graph by obtaining the difference between the highest and the lowest point in the graph. The fat layer thickness is then viewed by the attending physician using the B-mode display, wherein the reflected ultrasound echoes are displayed as two-dimensional images. The B-mode display is derived from the obtained A-mode data, in which the brightness of each point in the image depends on the signal amplitude of the reflected echo. Afterwards, an average fat layer thickness is calculated by obtaining measurements at random areas in the abdomen. Alternatively, measurements may be taken at only one position such as measuring the distance between the amniotic sac and the transducer surface. The computer then calculates a body fat percentage from the determined fat layer thickness using a software. The computer monitor then displays a body fat percentage of 35%, and correspondingly classified the patient as "OBESE." Afterwards, the computer automatically determines a plurality of appropriate health monitoring settings, which are sent and applied to the ultrasound device. The attending physician then switches back the ultrasound device to pulsed Doppler mode, and then performs fetal heart rate monitoring using the adjusted health monitoring setting.

In another embodiment, a patient visits a clinic for fetal heart rate monitoring. At the start of the session, the attending physician switches on two infrared sensors (IR receiver and IR transmitter) integrated into the ultrasound or Toco device. When IR waves are directed towards the fat tissue, the IR waves are reflected back to the IR receiver at different wavelengths. The reflected wavelengths are then recorded as an interferogram. Afterwards, the interferogram is converted into a spectral reading, the second derivative of which is used by a computer to obtain a body fat percentage using an equation. The computer monitor then displays a body fat percentage of 20%, and correspondingly classified the patient as "SLIM." Afterwards, the computer automatically determines a plurality of appropriate health monitoring settings, which are sent and applied to the ultrasound device. The attending physician then switches back the ultrasound device to continuous-wave or pulse Doppler mode, and then performs maternal pulse monitoring using the adjusted health monitoring setting. In some instances, the IR sensor is built into the Toco transducer which is then used as an independent source for the maternal pulse in order to prevent the ultrasound transducer from detecting the Doppler shift signal of the maternal blood vessel.

In some implementations, the classification and/or body fat measurement for adjustment of other medical monitoring devices may be done automatically through detection of skin contact by the measuring device. Thus, when an IR sensor contacts skin, immediate an automatic body classification is conducted. Further other sensors may be utilized to detect skin contact such as proximity sensors, temperature sensors, capacitance and other known skin detection methodologies and apparatus.

In yet another embodiment, a patient was brought to a hospital and was prescribed a uterine contraction monitoring session. At the start of the session, an attending physician initially sets the ultrasound Doppler sensor of an ultrasound device to pulse-echo mode. The attending physician then begins body fat layer thickness measurement using the ultrasound device in pulse-echo mode. The computer then generates an A-mode ultrasound reflection amplitude graph, from which the computer determines a fat layer thickness. To confirm the accuracy of the obtained fat layer thickness, the attending physician also obtains a measurement using two infrared sensors integrated into the ultrasound device. The fat layer thickness is calculated using the difference between the wavelength shifts of the top and bottom layer of the fat tissue. The IR sensor then transmits the calculated fat layer thickness to the physician's computer. The computer then calculates a body fat layer thickness. The two body fat layer thickness measurements obtained from the pulse-echo mode and from the IR sensors are then compared to determine if the two measurements more or less match. When the computer determines that the measurements more or less match, the measurements are compared to predetermined body fat thresholds, from which a body fat classification is derived. In case the two measured values differ to some extent, it might be preferable to use the average value of the two measured values of the fat layer thickness. Based on the determined matching body fat thresholds, the computer monitor then displays a body fat percentage of 32%, as well as the patient's classification, which is "NORMAL." The computer then automatically determines a plurality of appropriate health monitoring settings, sent and applied to the ultrasound device. The attending physician then switches back the ultrasound device to normal mode, then performs uterine contraction monitoring using the adjusted health monitoring settings.

In yet other embodiments, in the case when the body fat thickness obtained from the ultrasound and IR measurements do not match, both pulse-echo and IR methods are repeated until the measurements match.

The systems and methods disclosed can be used for hospital and home monitoring of fetal heart rate, for example, during labor and delivery.

The present disclosure is not intended to be restricted to the several exemplary embodiments described herein. Other variations that may be envisioned by those skilled in the art are intended to fall within the disclosure.

The invention claimed is:

1. A method for health monitoring comprising:
measuring a body fat composition by measuring body fat thickness via one or more sensors provided at an ultrasound measuring probe of a health monitoring device adapted for performing fetal or maternal monitoring;
classifying the measured body fat composition into one of a plurality of body fat categories, wherein the plurality of body fat categories comprise obese, normal, and slim;
adjusting operating parameters of the health monitoring device relevant for the fetal or maternal monitoring based on the classified body fat composition, wherein the operating parameters consist of a transmit energy setting, an amplifier gain adaptation setting, and a depth setting of the ultrasound measuring probe; and
performing a health monitoring measurement using the ultrasound measuring probe of the health monitoring device adjusted in the operating parameters,
wherein the health monitoring measurement comprises a fetal heart rate measurement.

2. The method of claim 1, wherein the body fat thickness is measured using an ultrasound Doppler sensor in a pulse echo mode.

3. The method of claim 1, wherein the body fat thickness is measured using an infrared transmitter and an infrared receiver.

4. The method of claim 1, wherein the body fat thickness is measured using a combination of an ultrasound Doppler sensor and infrared sensors.

5. The method of claim 1, wherein the body fat thickness is measured using a first ultrasonic array and the performing of the health monitoring measurement using the ultrasound measuring probe of the monitoring device is executed using a second ultrasonic array.

6. A system for health monitoring, comprising:
an ultrasound device in communication with a user device, wherein the ultrasound device is adapted for performing fetal or maternal monitoring;
the ultrasound device having a power source, communication module, memory, a processor and a transducer array, the transducer array having a plurality of transducer elements for receiving Doppler signals;
the ultrasound device operable to convert received ultrasound information for transmission to the user device;
wherein the user device comprises a processor, a display and a memory;
wherein the user device has instructions in the memory which, when executed, operates to:
receive the ultrasound information for use in measuring a body fat composition by measuring body fat thickness;
determine a body fat classification from the received ultrasound information, wherein determining the body fat classification comprises classifying the measured body fat composition into one of a plurality of body fat categories that comprise obese, normal, and slim; and
transmit the body fat classification to the ultrasound device;
wherein the ultrasound device modifies operating parameters of the ultrasound device for use in performing the fetal or maternal monitoring based upon the determined body fat classification, wherein the operating parameters consist of an ultrasound transmit energy setting, an amplifier gain adaptation setting, and a depth setting,
wherein the fetal or maternal monitoring comprises measuring a fetal heart rate.

7. The system of claim 6, wherein the ultrasound device operates in a first mode to determine fat layer thickness and a second mode for fetal or maternal monitoring.

8. The system of claim 7 wherein the first mode is a pulse-echo mode and the second mode is a pulse Doppler mode.

9. The system of claim 6 wherein the ultrasound device further comprises: at least one IR sensor, the at least one IR sensor of the ultrasound device operable to obtain a body fat thickness signal, and wherein the user device is operable to receive the body fat thickness signal and modify the body fat classification based upon the body fat thickness signal.

10. The system of claim 9 wherein the at least one IR sensor is an IR receiver and an IR transmitter.

11. The system of claim 10 wherein the user device stores instructions in the memory which, when executed, operates to:
determine an IR body fat thickness based upon the body fat thickness signal;
determine an ultrasound body fat thickness based upon the received ultrasound information;
calculate an average body fat thickness value based upon the ultrasound body fat thickness and the IR body fat thickness; and determine the body fat classification based upon the average: body fat thickness.

* * * * *